United States Patent [19]

Lieberman et al.

[11] Patent Number: 5,061,475

[45] Date of Patent: * Oct. 29, 1991

[54] COMPOSITION AND METHOD OF TREATMENT OF ARTHRITIS AND RELATED DISEASES WITH HOLMIUM-166 RADIONUCLIDES

[75] Inventors: Ephraim Lieberman, Suffern; Maurice E. Bordoni, Westtown; Alfred K. Thornton, New Hampton, all of N.Y.

[73] Assignee: Cadema Medical Products, Inc., Middletown, N.Y.

[*] Notice: The portion of the term of this patent subsequent to Jun. 21, 2005 has been disclaimed.

[21] Appl. No.: 372,628

[22] Filed: Jun. 28, 1989

Related U.S. Application Data

[63] Continuation-in-part of Ser. No. 007,597, Jan. 28, 1987, Pat. No. 4,849,209, which is a continuation-in-part of Ser. No. 742,402, Jun. 7, 1985, Pat. No. 4,752,464.

[51] Int. Cl.$^5$ .................... A61K 43/00; A61B 6/00
[52] U.S. Cl. .......................... 424/1.1; 600/3; 600/4; 252/625; 252/635; 514/825
[58] Field of Search .................. 424/1.1; 600/3, 4; 252/625, 635

[56] References Cited

U.S. PATENT DOCUMENTS

| | | | |
|---|---|---|---|
| 3,961,038 | 6/1976 | Benes | 424/1.1 |
| 4,752,464 | 6/1988 | Lieberman et al. | 424/1.1 |
| 4,758,429 | 7/1988 | Gordon | 600/5 X |
| 4,849,209 | 7/1989 | Lieberman et al. | 424/1.1 |
| 4,889,707 | 12/1989 | Day et al. | 424/1.1 |
| 4,897,254 | 1/1990 | Simon et al. | 424/1.1 |
| 4,898,724 | 2/1990 | Simon et al. | 424/1.1 |
| 4,906,450 | 3/1990 | Lieberman et al. | 424/1.1 |
| 4,915,932 | 4/1990 | McLaren et al. | 424/1.1 |

OTHER PUBLICATIONS

Sledge et al., Radiation Synovectony, No. 152, (1984), pp. 37–40.
Sledge et al., Arthritis and Rheumatism, vol. 20 (7), pp. 1334–1342 (1977).
Hnatowich et al., The Journal of Nuclear Medicine, vol. 19, No. 3, 303–308 (1978).

*Primary Examiner*—Richard D. Lovering
*Assistant Examiner*—John M. Covert
*Attorney, Agent, or Firm*—Leonard Bloom

[57] ABSTRACT

An aggregate suspension containing holmium-166 hydroxide and a carrier (such as a particulate ferric hydroxide) is injected into a patient's anesthetized joint (such as a knee joint or hip joint) for the treatment of inflamed synovial tissues such as present in arthritis, especially rheumatoid arthritis. The aggregate suspension is in a range of particle sizes from 1 to 40 microns. The holmium-166-containing suspension treats the synovial tissues, whereby radiation synovectomy takes place.

46 Claims, No Drawings

COMPOSITION AND METHOD OF TREATMENT OF ARTHRITIS AND RELATED DISEASES WITH HOLMIUM-166 RADIONUCLIDES

CROSS-REFERENCE TO RELATED APPLICATIONS

This application is a continuation-in-part of co-pending application Ser. No. 007,597 filed Jan. 28, 1987, (which issued on July 18, 1989 as U.S. Pat. No. 4,849,209), which in turn is a continuation-in-part of application Ser. No. 742,402 filed June 7, 1985 (which issued on June 21, 1988 as U.S. Pat. No. 4,752,464) the disclosures of which are incorporated by reference herein in their entirety.

FIELD OF THE INVENTION

The present invention relates to radioactive compounds, methods for the preparation thereof and a method for the treatment of arthritis and related diseases, including rheumatoid arthritis, and osteoarthritis.

BACKGROUND OF THE INVENTION

Inflammatory diseases, which include inflammatory synovitis, arthritis generally, rheumatoid arthritis more specifically, and other diseases including osteoarthritis are leading causes of losses in time and earnings in the United States. More specifically, approximately six million of all arthritis sufferers are afflicted with rheumatoid arthritis. Of these, if past trends continue, over fifty percent (50%) ultimately will have involvement of the knee joint; over eighty percent (80%) will have involvement with the hand joint; and somewhat smaller percentages will have involvement of other joints such as the ankle, elbow, shoulder, hip and wrist.

Rheumatoid arthritis and other forms of inflammatory disease are believed to be autoimmune diseases wherein parts of the body are attacked by antibodies manufactured in the body. These antibodies may be produced in response to viruses present in the body. While the mechanism for rheumatoid arthritis is not defined, it is a systemic disease. When the disease is active, the erythrocyte sedimentation rate (ESR) is elevated and the blood tests positive for rheumatoid factor.

A source of disability for the sufferer of rheumatoid arthritis is an inflammatory response, of unknown origin, in the synovium, or lining, of an afflicted joint. Chronic inflammation of synovial tissues, or synovitis, may lead to pannus formation and, eventually, to destruction of the joint cartilage.

Presently, the primary, method of treating rheumatoid arthritis is by use of orally ingested or otherwise systemically administered compounds directed at blocking the inflammatory process. These compounds include aspirin, penicillamine, gold salts, and many other ethical drugs. Unfortunately, these attempts are often unsuccessful, and the relief provided is temporary at best.

The primary alternative mode of treatment of rheumatoid arthritis is the surgical excision of the inflamed synovium in a procedure known as surgical synovectomy. In this procedure the abnormal synovium and pannus formation are surgically removed. While, in many cases, this procedure proves to arrest the disease, it also has a significant number of drawbacks and limitations. Among these are limitations on complete removal of the inflamed synovium, the risks and dangers inherent in the operation itself, and the required lengthy recovery period, much of which is spent in the hospital.

In order to overcome these problems, attempts have been made to destroy the diseased synovium by the performance of a procedure known as radiation synovectomy. Intra-articular injection of colloidial gold-198 ($^{198}$Au) has been reported to abate inflamed synovium (Fellinger et al, 33 WEIN Z. INN, Med. 351, (1952) and Ansell et al, 22 Ann. Rheum. Dis. 435 (1963)). Unfortunately, this procedure is disadvantageous due to the small particle size of the gold colloid utilized and the high energy gamma photons emitted during radioactive decay (gamma emission). This emission poses dangers to the patient by increasing the whole body dose, thereby exposing healthy tissue to radiation, and posing substantial problems in protecting hospital personnel from radiation exposure.

The use of other radionuclides has also been attempted in radiation synovectomy. These radionuclides include Erbium-169 ($^{169}$Er) as reported in Menkes et al, 36 Ann. Rheum. Dis. 254 (1977); Rhenium-186 ($^{186}$Re) as reported in Deckart et al, 3 Radiobiol, Radiother 363 (1979) and in DelBarre et al, 2 Nouv. Presse. Med 1372 (1973); Phosphorus-32 ($^{32}$P) as reported in Wenston et al, 14 J. Nuc. Med 886 (1973), and Yttrium-90 ($^{90}$Y) as reported in Gumpel et al, 48 Br. J. Radiol. 377 (1975).

Each of these radionuclides ($^{169}$Er, $^{186}$Re, $^{32}$P, $^{198}$Au, and $^{90}$Y) has proven disadvantageous due to either the long physical half-life of the particular radionuclide involved, the small particle size of the system, and/or the occurrence of significant amounts of radioactivity leaking from the affected joints and associated chromosomal aberrations in the lymphocytes of the patient. (See also; Oka et al, 17 Acta Rheum. Scand. 148 (1971) and Virkkunen et al, 13 Acta Rheum, Scand, 1967.)

Currently, the preferred radionuclide in the prior art is Dysprosium-165 ($^{165}$Dy) hydroxide in suspension with ferric hydroxide. Sledge et al, 182 Clin. Ortho, and Rel. Research 37 (1984) (hereinafter referred to as "Sledge"). Sledge has found that the use of $^{165}$Dy hydroxide in suspension with ferric hydroxide is more advantageous in performing radiation synovectomy than the aforementioned radionuclides. Sledge has identified as the advantages of $^{165}$Dy hydroxide with ferric hydroxide: (1) proper energy range of beta emissions; (2) formation of a larger colloid which reduces the potential of leakage; and (3) an extremely short half-life of 2.3 hours which further reduces the effects of potential leakage.

These are qualities which the prior art has reported to be desirable when selecting an appropriate radioactive compound for use in radiation synovectomy (See also Sledge et al, 20 Arthritis Rheum 1334 (1977), Noble et al, 65A J. Bone Joint Surg. 381 (1983), and Deckert and Gumpel, both supra).

While the short half-life of $^{165}$Dy hydroxide in suspension with ferric hydroxide is one of the major characteristics noted by Sledge and the other references which make it such a desirable candidate for radiation synovectomy, this short half-life also proves to be a major limitation to its practical use. $^{165}$Dy requires a nuclear reactor in order to be produced. It also must be injected within a few hours of its manufacture to be effective. As a result, its utility in radiation synovectomy is severely limited by geographical and distribution factors.

Accordingly, there remains a need for an effective radioactive compound that will have both utility in radiation synovectomy and will be able to be prepared in, and distributed from, a central location using existing transportation channels.

SUMMARY OF THE INVENTION

Accordingly, it is the primary object of this invention to provide radioactive isotopes in a form useful in the treatment of inflamed synovial tissues, generally, and, more particularly, useful for radiation synovectomy in the treatment of arthritis, especially rheumatoid arthritis of the knee.

It is still another object to provide radioactive compounds for the treatment of inflamed synovial tissues generally, such as present in arthritis, and more particularly in rheumatoid arthritis, which can be prepared at, and distributed from, a central location utilizing existing transportation channels.

It is still another object of this invention to provide methods for the preparation of radioactive compounds useful in radiation synovectomy for the treatment of inflamed synovial tissues.

It is another object of this invention to provide methods for the treatment of arthritis generally and, more particularly, rheumatoid arthritis.

It is another object of the invention to provide compositions for the treatment of inflamed synovial tissues by injection at the site of the inflamed synovial tissues.

These and other objects are accomplished by one or more embodiments made in accordance with the teachings of the present invention.

In accordance with the teachings of the present invention we have discovered that compounds containing holmium-166 radionuclide are useful for treating inflamed synovial tissues generally, and useful for treating arthritis and rheumatoid arthritis more particularly, by injection near the site of the inflamed synovial tissues, whereby radiation synovectomy takes place.

Further in accordance with the teachings of the present invention, precipitated compounds of holmium-166 are provided in aggregation with precipitated metal hydroxide carriers, wherein the particulate aggregate has particle sizes substantially in the range of 1-40 microns.

In further accordance with the teachings of the present invention, radioactive compounds including holmium-166 are provided for the treatment of inflamed synovial tissues, where the compounds can be prepared at and distributed from a central location utilizing existing channels of transportation.

In further accordance with the teachings of the present invention, methods are provided for the preparation of radioactive compounds containing holmium-166 useful in radiation synovectomy for the treatment of inflamed synovium generally, for arthritis more particularly, and for rheumatoid arthritis still more particularly.

Further in accordance with the teachings of the present invention, there is provided a method employing holmium-166 for the treatment of inflamed synovium due to arthritis and, more particularly, rheumatoid arthritis.

In accordance with the invention, holmium-166 radioactive compounds have utility in radiation synovectomy for the treatment of inflamed synovial tissues such as present in rheumatoid arthritis. In accordance with the teachings of this invention, desired aspects of holmium-166 treatment include: safety; effectiveness; a relatively large particulate carrier; beta emissions of a desired energy; a half-life that permits distribution through normal distribution transportation channels; and very low levels of other types of energies (e.g. gamma radiation) whereby such low levels preclude damage to healthy tissue. More specifically, the half-life is both long enough to permit the compound's central preparation and distribution and short enough to reduce the deleterious effects of potential leakage.

The nature and substance of the present invention, as well as its objectives and advantages, will be more clearly perceived and fully understood by reference to the following description and claims.

DESCRIPTION OF PREFERRED EMBODIMENTS

The radioactive compounds of the present invention include $_{67}Ho^{166}$ (holium-166) nuclide. Holmium-166 has a half-life of 26.8 hours [See Handbook of Chemistry and Physics, 62nd Edition, Chemical Rubber Corporation (1981-1982) at B-302]. The 26.8 hour half-life allows for sufficient time following production of the isotope in a nuclear reactor for the preparation and distribution of the finished compound using existing transportation channels. Holmium-166 has beta energies up to 1.84 MeV with approximately 85% of the beta particles being in the 1.76-1.84 MeV energy range.

While, during decay, holmium-166 does emit a low energy KeV gamma photon, this emission is not disadvantageous due to its low energy. Additionally, while holmium-166 also has a high energy gamma emission component, this emission component is less than 1% in abundance. Therefore, the totality of the gamma emissions is relatively low in energy, and the gamma emissions do not present problems to either the patient or hospital personnel.

$_{67}Ho^{165}$ (holmium-165), from which holmium-166 is obtained, has a natural abundance of 100%. The activation cross-section for production of holmium-166 from holmium-165 by thermal neutrons permits substantial quantities of holmium-166 to be produced in a nuclear reactor.

The particles emitted from the radioactive decay of holmium-166 have an average soft tissue penetration of only approximately 3.3 mm and a maximum soft tissue penetration of only approximately 9 mm. The relatively low soft tissue penetration resulting from holmium-166 decay results in relatively low leakage of radiation away from the site of administration. More particularly, the beta energy decay makes holmium-166 particularly attractive for radiation synovectomy of inflamed synovial tissues, particularly a diseased arthritic knee. We have found that holmium-166 in certain chemical compounds also forms a substantially large colloid having particle sizes greater than one micron which further reduces the potential for leakage.

The preferred form of holmium-166 is the hydroxide. However, it is to be understood that the holmium-166 radionuclide can be suitably formed as any colloidal particle provided that it is not toxic when administered to a patient by injection at the site of inflamed synovial tissues.

The preferred radioactive compound of the present invention is particulate holmium-166 hydroxide in aggregation with a carrier of ferric hydroxide macroaggregate (FHMA). It is to be noted that other materials would also suffice, such as holmium-166 hydroxide in aggregation with a carrier of aluminum hydroxide macroaggregate (AHMA), or holmium-166 hydroxide formed in the presence of other soluble transition metal chlorides (i.e. bismuth and chromium, to name but two) which when converted to the hydroxide forms a particulate metallic hydroxide.

In that the particle size of the administered radioactive materials has a major impact on the leakage rate, the preferred radioactive material has a minimum particle size of 1 micron. As practiced and prepared herein, the holmium-166-ferric-hydroxide aggregate has particles ranging in size from substantially 1 micron to 40 microns.

The carrier for holmium-166 can also be derived from other inorganic materials, and can be derived from organic materials as well. Suitable other inorganic carriers include aluminum hydroxide.

The particulate aggregate of the holmium-166 compound and the particulate carrier is generally administered to the site of synovium inflammation by injection of an aggregate suspension in an aqueous carrier.

While not required, it is preferred that the aggregate suspension further contain a stabilizing ingredient to aid in preventing agglomeration of the particles in the preparation. The stabilizing agents include high molecular weight polymers such as polyvinyl pyrrolidone (PVP). Other high molecular weight polymers such as a polyoxypropylene-polyoxyethylene block-copolymer may be combined with the holmium-166 macroaggregate.

The radioactive holmium-166 hydroxide aggregate suspension is prepared by a method comprising, first obtaining holmium in a suitable form. In the preferred embodiment, the starting material is holmium-165 as a natural oxide, $(_{67}Ho^{165})_2O_3$. This suitable form of holmium is then irradiated in a nuclear reactor to obtain the desired species of the compound. In the preferred embodiment, this reaction is:

$$_{67}Ho^{165} + neutrons \rightarrow {}_{67}Ho^{166} \text{ as } (_{67}Ho^{166})_2O_3$$

Following irradiation, the radionuclide is then dissolved in dilute aqueous hydrochloric acid to produce a chloride form of the radionuclide. In the preferred embodiment, this dissolution of the irradiated target oxide proceeds by the following equation:

$$(_{67}Ho^{166})_2O_3 + 6HCl \text{ (dilute)} \rightarrow 2(_{67}Ho^{166})Cl_3 + 3H_2O.$$

To this aqueous solution is then added a solution of a transition metal chloride. In the preferred embodiment, and for purposes of illustration herein, the transition metal chloride described is ferric chloride ($FeCl_3$). However, it is to be understood that the transition metal chloride utilized may alternatively be aluminum chloride ($AlCl_3$), bismuth chloride ($BiCl_3$), chromium chloride ($CrCl_3$), cupric chlorite ($CuCl_2$), manganese chloride ($MnCl_2$), or stannous chloride ($SnCl_2$). Sodium hydroxide is then added to this solution in an amount sufficient to adjust the pH of the solution to a value of from 4 to 9. In the preferred embodiment, the reaction then proceeds according to the following equation:

$$(_{67}Ho^{166})Cl_3 + FeCl_3 + 6NaOH \rightarrow (_{67}Ho^{166})(OH)_3 + Fe(OH)_3 + 6NaCl.$$

The product is an aggregated precipitate of the metal (which in this case is iron) and holmium-166 hydroxides which are intimately coprecipitated. The particle size of this precipitate ranges from 1 to 40 microns.

To prepare an aggregated precipitate of the invention for use for the treatment of a patient, one of several methods, well known to those skilled in the art, may be employed. Also, methods well known in the art (for testing for pyrogens) may also be employed.

It is also to be understood by those skilled in the art that certain agents may be added to the original holmium-166 chloride solution. For purposes of illustration only, prior to the addition of the sodium hydroxide, a stabilizing matrix such as polyvinyl pyrrolidone (PVP) is added to the original holmium-166 chloride solution. This stabilizer is added to the suspension to help in maintaining discrete particles (separate particles) to prevent agglomeration of the aggregate.

Suspended in an aqueous carrier, the holmium-166 hydroxide aggregate suspension is then ready for being administered to the patient. At this time, the holmium-166 hydroxide preparation may be immediately administered or, if desired, it may be suitably packaged and shipped to its ultimate point of use by utilization of existing channels of transportation such as automobiles, trucks, buses, helicopters, airplanes, etc.

Administration of the holmium-166 hydroxide aggregate suspension preparation is performed by methods well known to those skilled in the art. By way of example, the preferred method of administration to the synovial tissues of the knee, hip and/or shoulder of an individual is by intra-articular injection.

EXAMPLE I

An injection to a knee to treat the synovia of the knee joint may take place in the patient's room or in any other suitable location with monitoring by hospital personnel. The patient is in the supine position.

Prior to injection, the skin of the knee is treated with an antiseptic, e.g. washed with, preferably, a betadine solution. A local anesthetic, e.g. one percent lidocaine hydrochloride, is instilled in the skin and subcutaneous tissue.

A 3-way stopcock/needle assembly is utilized to administer the treating compound. A 19 gauge needle is employed. A suspension of holmium-166 hydroxide with a ferric hydroxide macroaggregate is injected into the knee joint space using a standard lateral approach well known to those skilled in the art. The needle and needle tract are cleansed by flushing with 1% lidocaine hydrochloride through the 3-way stopcock assembly as the needle is withdrawn. The knee is moved through a flexion-extension arc and then immobilized in full extension. The patient is confined to bed for approximately 24 hours to minimize movement and minimize leakage of radioactivity from the joint.

It will be understood by those skilled in the art that the exact amount of radioactive compound to administer as a therapeutic agent is also within the skill of the practitioner. However, by way of example, if the practitioner desires to deliver a dose of 10,000 rads to the afflicted synovium, he must merely use classic techniques, well known to those skilled in the art, for beta dosimetry that assume a homogenous distribution of radioactivity in the synovium without extra-articular leakage in order to arrive at quantity of radioactive compound to administer. We have found that 17.5 mCi of the holmium-166 hydroxide preparation will deliver approximately 10,000 rads to the diseased synovium in a knee joint.

The production of the radioactive compounds of the present invention requires use of a nuclear reactor. However, production of holmium-166 is relatively simple and inexpensive. The half-life of holmium-166, which is 26.8 hrs., facilitates distribution from the production site and eliminates logistic problems, as well as problems associated with the ultimate disposal of the compounds, thereby facilitating the widespread commercialization of this invention.

Thus, this invention provides novel radioactive compounds; a method for the preparation of such compounds; and a method that is useful in the treatment of inflamed synovia such as present in arthritis and, more particularly, rheumatoid arthritis, and for alleviating the pain and suffering associated therewith.

While specific embodiments of the present invention have been shown and described to illustrate inventive principles, it is to be understood that such showing and description have been offered only by way of example and are not limiting.

It will be understood that various changes in the details and steps, which have been herein described to explain the nature of the invention, may be made by those skilled in the art within the principles and scope of the invention as expressed in the appended claims.

What is claimed is:

1. A radioactive composition for the treatment of arthritis comprising a suspension containing particles having a minimum size of one micron, said suspension including particles containing holmium-166.

2. A radioactive composition for the treatment of arthritis comprising a suspension containing particles having a minimum size of one micron, said suspension including particles containing holmium-166 and a particulate carrier.

3. The radioactive composition described in claim 2 wherein said particulate carrier includes ferric hydroxide.

4. The radioactive composition described in claim 2 wherein said particulate carrier includes aluminum hydroxide.

5. A radioactive composition for the treatment of rheumatoid arthritis comprising a suspension containing particles having a minimum size of one micron, said suspension including particles containing holmium-166 in an amount effective for the treatment of rheumatoid arthritis.

6. A radioactive composition for the treatment of rheumatoid arthritis comprising a suspension containing particles having a minimum size of one micron, said suspension including particles containing holmium-166 in an amount effective for the treatment of rheumatoid arthritis and a particulate carrier.

7. A composition for the treatment of inflamed synovial tissues including particles having a minimum size of one micron, the particles containing holmium-166 and a carrier suitable for injection at the site of the inflamed synovial tissues.

8. The radioactive composition described in claim 7 wherein said carrier includes a metallic hydroxide.

9. The radioactive composition described in claim 7 wherein said carrier includes a metallic hydroxide selected from the group consisting of bismuth hydroxide, chromium hydroxide, cupric hydroxide, manganese hydroxide, and stannous hydroxide.

10. The radioactive composition described in claim 7 wherein said carrier includes ferric hydroxide.

11. The radioactive composition described in claim 7 wherein said carrier includes aluminum hydroxide.

12. A method of conducting radiation synovectomy including the step of injecting a composition into a patient in the vicinity of synovial tissues to be treated, wherein the injected composition contains particles which include holmium-166 said particles having a minimum size of one micron.

13. The method described in claim 12 wherein the injected composition contains a suspension of particles including holmium-166 and a carrier.

14. The method described in claim 12 wherein the injected composition contains a suspension of particles including holmiun-166 and a metallic hydroxide carrier.

15. The method described in claim 14 wherein said metallic hydroxide carrier is selected from the group consisting of bismuth hydroxide, chromium hydroxide, cupric hydroxide, manganese hydroxide, and stannous hydroxide.

16. The method described in claim 12 wherein the injected composition contains a suspension of particles including holmium-166 and a monoclonal antibody carrier.

17. A method for the localized treatment of synovial tissue of a joint, comprising the steps of:
preparing an aggregated suspension containing particles, the particles having a minimum size of one micron, including particles containing holmium-166;
obtaining a solution of a local anesthetic;
placing the holmium-166 containing suspension in a needle assembly;
treating the skin surrounding the joint with an antiseptic;
instilling the anesthetic solution in the skin and the subcutaneous tissues surrounding the joint;
injecting the holmium-166-containing suspension into the joint near the synovial tissues thereof;
moving the joint through a flexion-extension arc; and
immobilizing the joint in full extension for a predetermined period of time to permit treatment of the synovial tissues, by the holmium-166-containing suspension, to take place.

18. A method for the treatment of synovial tissue of a joint comprising injecting, to the joint, a therapeutically effective quantity of an aggregated suspension containing particles, the particles having a minimum size of one micron, including particles containing holmium-166.

19. A method for the localized treatment of synovial tissue of a joint, comprising the steps of:
preparing an aggregated suspension containing particles, the particles having a minimum size of one micron, including particles containing holmium-166;
obtaining a solution of a local anesthetic;
placing the holmium-166-containing suspension in a needle assembly which includes a needle, a needle tract, and a three-way stopcock;
treating the skin surrounding the joint with an antiseptic;
instilling the anesthetic solution in the skin and the subcutaneous tissues surrounding the joint;
injecting the holmium-166 containing suspension into the joint near the synovial tissues thereof;

cleansing the needle and needle tract by flushing with the anesthetic solution through the stopcock assembly as the needle is withdrawn from the patient;

moving the joint through a flexion-extension arc; and immobilizing the joint in full extension for a predetermined period of time to permit treatment of the synovial tissues by the holium-166-containing suspension to take place.

20. A method for the localized treatment of an arthritic joint, comprising the steps of:

preparing an aggregated suspension containing particles, the particles having a minimum size of one micron, including particles containing holmium-166;

obtaining a solution of a local anesthetic;

placing the holmium-166-containing suspension in a needle assembly;

treating the skin surrounding the joint with an antiseptic;

installing the anesthetic solution in the skin and the subcutaneous tissues surrounding the joint;

injecting the holmium 166-containing suspension into the joint near the synovial tissues thereof;

moving the joint through a flexion-extension arc; and immobilizing the joint in full extension for a predetermined period of time to permit treatment of the arthritic joint by the holmium-166-containing suspension to take place.

21. A method for the treatment of an arthritic joint comprising injecting, to the joint, a therapeutically effective quantity of an aggregated suspension containing particles, the particles having a minimum particle size of one micron, including particles containing holmium-166.

22. A radioactive composition for use in treating inflamed synovial tissues comprising an injectable suspension containing particles having a minimum size of one micron, said suspension including particles containing holmium-166, said composition suitable for injection at the site of the inflamed synovial tissues.

23. The radioactive composition described in claim 22, further including a carrier compatible with the tissues undergoing treatment.

24. The radioactive composition described in claim 22 wherein said carrier is a metallic hydroxide.

25. The radioactive composition described in claim 22 wherein said carrier is a monoclonal antibody.

26. A radioactive composition for the treatment of arthritis comprising a particulate aggregate containing particles having a minimum size of one micron, said particulate aggregate including particles of particles containing holmium-166.

27. A radioactive composition for the treatment of arthritis comprising of a particulate aggregate containing particles having a minimum size of one micron, said particulate aggregate including particles of particles containing holmium-166 and a particulate carrier.

28. The radioactive composition described in claim 29 wherein said particulate carrier includes ferric hydroxide.

29. The radioactive composition described in claim 27 wherein said particulate carrier includes aluminum hydroxide.

30. A radioactive composition for the treatment of rheumatoid arthritis comprising a particulate aggregate containing particles having a minimum size of one micron, said particulate aggregate including particles containing holmium-166 in an amount effective for the treatment rheumatoid arthritis.

31. A radioactive composition for the treatment of rheumatoid arthritis comprising a particulate aggregate containing particles having a minimum size of one micron, said particulate aggregate including particles containing holmium-166 in an amount effective for the treatment of rheumatoid arthritis and a particulate carrier.

32. A composition for the treatment of arthritis including particles, the particles having a minimum size of one micron, including particles containing holmium-166 and a particulate carrier suitable for injection at the site of the arthritis.

33. A composition for the treatment of rheumatoid arthritis including particles, the particles having a minimum size of one micron, including particles containing holmium-166 and a particulate carrier suitable for injection at the site of the rheumatoid arthritis.

34. A composition for the treatment of inflamed synovial tissues including particles, the particles having a minimum size of one micron, including particles containing holmium-166 and a particulate carrier suitable for injection at the site of the inflamed synovial tissues.

35. The radioactive composition described in claim 34 wherein said carrier includes a metallic hydroxide.

36. The radioactive composition described in claim 34 wherein said carrier includes ferric hydroxide.

37. The radioactive composition described in claim 34 wherein said carrier includes aluminum hydroxide.

38. A method of conducting radiation synovectomy including the step of injecting an aggregate composition containing particles, the particles having a minimum size of one micron into a patient in the vicinity of synovial tissues to be treated, wherein the injected aggregate composition contains particles which include holmium-166.

39. The method described in claim 38 wherein the injected composition contains an aggregate of particles containing holmium-166 and a particulate carrier.

40. The method described in claim 38 wherein the injected composition contains an aggregate of particles containing holmium-166 and a particulate metallic hydroxide carrier.

41. The method described in claim 38 wherein the injected composition contains an aggregate of particles containing holmium-166 and a monoclonal antibody carrier.

42. A radioactive composition for use in treated inflamed synovial tissues comprising an injectable particulate aggregate containing particles having a minimum size of one micron, said particulate aggregate including particles containing holmium-166, said composition suitable for injection at the site of the inflamed synovial tissues.

43. The radioactive composition described in claim 42 including a carrier compatible with the tissues undergoing treatment.

44. The radioactive composition described in claim 42 wherein said carrier is a monoclonal antibody.

45. The radioactive composition described in claim 42 including a particulate carrier compatible with the tissues undergoing treatment.

46. The radioactive composition described in claim 45 wherein said carrier is a particulate metallic hydroxide.

* * * * *